United States Patent
Suorsa et al.

(10) Patent No.: US 6,287,261 B1
(45) Date of Patent: Sep. 11, 2001

(54) FOCUSED ULTRASOUND TRANSDUCERS AND SYSTEMS

(75) Inventors: Veijo T. Suorsa, Sunnyvale; Dennis Mendoza, Tracy; Richard Bautista, Palo Alto, all of CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/362,630

(22) Filed: Jul. 21, 1999

(51) Int. Cl.[7] ........................................................ A61B 8/14
(52) U.S. Cl. .................................................................. 600/459
(58) Field of Search ........................ 600/437, 459, 600/446, 463; 73/620, 625

(56) References Cited

U.S. PATENT DOCUMENTS

| | | | |
|---|---|---|---|
| 3,958,559 | | 5/1976 | Glenn et al. ......................... 128/2 V |
| 4,246,791 | * | 1/1981 | Glenn ..................................... 73/620 |
| 4,248,090 | * | 2/1981 | Glenn ..................................... 73/620 |
| 4,325,381 | * | 4/1982 | Glenn ................................... 600/437 |
| 4,572,201 | * | 2/1986 | Kondo et al. ........................ 600/437 |
| 4,762,002 | * | 8/1988 | Adams .................................... 73/625 |
| 5,402,792 | * | 4/1995 | Kimura ................................. 600/463 |
| 5,520,189 | * | 5/1996 | Malinowski et al. ................. 600/459 |
| 5,596,989 | * | 1/1997 | Morita .................................. 600/446 |

FOREIGN PATENT DOCUMENTS 3441 684 A1    11/1984  (DE) ............................... H04R/7/04

* cited by examiner

*Primary Examiner*—Marvin M. Lateef
*Assistant Examiner*—Ali M. Imam
(74) *Attorney, Agent, or Firm*—Townsend and Townsend and Crew, LLP

(57) ABSTRACT

The present invention provides ultrasound transducers, and imaging assemblies and catheters employing such transducers, that provide improved imaging capabilities. In one embodiment, an ultrasound imaging assembly (50) includes a housing having a distal end (56), a proximal end (57) and a longitudinal axis. A transducer element (54) is included having an outer face. The outer face has a first radius of curvature along a first axis and a second radius of curvature along a second axis. The transducer element is operably attached to the distal end to position the first axis to be generally parallel to the longitudinal axis to provide improved cross-plane resolution.

33 Claims, 8 Drawing Sheets

In-plane (x)
Peak = 0.046 Vpp
Focal Width = 0.14 mm; Focal Length>=-46.85 mm
Scan starts at 0.30 mm Cross - Plane (Y)
Peak = 0.02414 Vpp
Focal Width = 0.26 mm; Focal Length>= -2.20 mm
Scan starts at 0.30 mm

FOCUSED ULTRASOUND TRANSDUCERS AND SYSTEMS

BACKGROUND OF THE INVENTION

The present invention relates generally to ultrasonic imaging catheters, and more particularly, to ultrasonic transducers providing improved resolution for such catheters.

Intravascular imaging of blood vessels and surrounding tissues continues to be of great benefit in a wide range of medical fields. A particularly successful design for an intravascular imaging catheter 10 is shown in FIGS. 1A and 1B. Catheter 10 employs a rotatable imaging assembly 12 having a distal end 16 and a proximal end. An ultrasound transducer 14 is attached to distal end 16. The proximal end is operably attached to a flexible drive cable (not shown). Transducer 14 typically is elliptical in shape with a flat outer face. The transducer outer face has its major axis aligned with a longitudinal axis 20 of the imaging assembly 12. In other cases, the transducer 14 is round in shape with a flat outer face as shown in FIG. 1C.

During operation, a flexible sheath 18 is inserted into a patient with the drive cable and imaging assembly 12 disposed within sheath 18. The imaging assembly 12 typically is rotated within sheath 18 during transmission of ultrasound signals into the patient. During rotation of imaging assembly 12, transducer 14 projects ultrasound signals into a 360 degree image plane. The image plane has an in-plane or X-plane component 22 created primarily by the rotation of transducer 14. The image plane also has a cross-plane or Y-plane component 24 created primarily by the length of the major axis of transducer 14 for the transducer shown in FIG. 1B. The transducer element 14 is connected to electronics, typically maintained outside the patient's body, to produce a video image of at least a portion of the image plane by well-known techniques.

To produce images, it is desirable to have ultrasound signals transmitted by transducer 14 pass through sheath 18 and reflect off of tissue or fluids. However, a portion of the ultrasound signals transmitted by the transducer 14 typically are reflected by the sheath 18. Another portion of the ultrasound signals pass through sheath 18, but are refracted by sheath 18 during passage.

Due at least in part to the sheath effects on the ultrasound signal and to the shape of the transducer, ultrasound signals typically have a different in-plane profile than a cross-plane profile. The in-plane profile typically is narrower or tighter than the cross-plane profile. This can be seen by comparing FIG. 2A (depicting an in-plane profile 26 for a round transducer) with FIG. 2B (depicting a cross-plane profile 28 for a round transducer). Further, the in-plane profile 26 has a focal length that is shorter compared to the focal length in the cross-plane profile 28. As a result, the transducer 14 has better lateral resolution in the in-plane direction 22 than in the cross-plane direction 24.

It is desirable, therefore, to produce a tighter beam profile in the cross-plane direction so that the focal point is closer to the transducer surface. Improved cross-plane lateral resolution will result. It is further desirable to provide a more circular or symmetrical cross-section for the ultrasound signal profile, so that lateral resolution is similar for both the in-plane and cross-plane.

SUMMARY OF THE INVENTION

The present invention provides ultrasound transducers, and imaging assemblies and catheters employing such transducers, that provide improved imaging capabilities. For example, the present invention provides improved lateral resolution as a result of the positioning of the transducer on the imaging assembly and/or the curvature profile of the transducer outer face. This produces a tighter imaging signal in the cross-plane direction, thereby improving lateral resolution.

In one embodiment, the present invention provides an ultrasound imaging assembly. The imaging assembly includes a housing having a distal end, a proximal end, and a longitudinal axis. The assembly includes a transducer element having a generally elliptical outer face which defines a major axis and a minor axis. The transducer element is operably attached to the distal end to position the minor axis to be generally parallel to the longitudinal axis. In this manner, a tighter cross-plane beam profile is produced due to the minor axis being generally parallel to, i.e. generally aligned with, the longitudinal axis of the imaging assembly.

In one aspect, the outer face of the transducer element is generally oval shaped. It will be appreciated by those skilled in the art, that other transducer shapes may be used within the scope of the present invention. In another aspect, the outer face is generally flat.

In one aspect, the outer face has a first radius of curvature along the minor axis and a second radius of curvature along the major axis. Preferably, the second radius of curvature is greater than the first radius of curvature. In this manner, the transducer element has a tighter radius of curvature in the cross-plane direction to provide a greater focussing effect in the cross-plane direction compared to the focussing effect in the in-lane direction. A tighter cross-plane beam profile will result compared to the device shown in FIG. 1. Alternatively, the first and second radii of curvature are generally equal.

In one aspect, the proximal end is adapted to be coupled to a drive cable. In this manner, the drive cable can operate to rotate the imaging assembly. In another aspect, a matching layer or multiple matching layers are operably attached to the outer face of the transducer element. In this manner, improved efficiency and band-width can result.

In one aspect, the transducer element is a tapered focus transducer element. Alternatively, the transducer element is a true focus transducer element. Preferably, the transducer element is selected from a group of materials consisting of piezoplastics, piezocomposites, and piezoceramics.

In one particular aspect, the transducer element is adapted to propagate an ultrasound signal in response to electrical input. The ultrasonic beam includes an in-plane signal component that is generally perpendicular to the longitudinal axis, and a cross-plane signal component that is generally parallel to the longitudinal axis. The in-plane signal component has an in-plane focal length that is generally equal to a cross-plane focal length of the cross-plane signal component. In one aspect, the in-plane focal length is between about 0.25 mm and about 2.5 mm. Similarly, the cross-plane focal length is between about 0.25 mm and about 2.5 mm. In one particular aspect, the outer face has a shape and radius of curvature profile so that the ultrasound signal has a generally circular cross-sectional shape at a prescribed distance, for example between about 0.25 mm and about 2.5 mm, from the distal end.

The invention further provides an ultrasound imaging assembly which includes a housing having a distal end, a proximal end and a longitudinal axis. A transducer element having an outer face is included and coupled to the housing. The outer face has a first radius of curvature along a first axis and a second radius of curvature along a second axis. The transducer element is operably attached to the distal end to position the first axis to be generally parallel to the longitudinal axis. In one aspect, the second radius of curvature is greater than the first radius of curvature. Alternatively, the first and second radii of curvature are generally equal.

In one aspect, the first axis is a major axis of the outer face and the second axis is a minor axis of the outer face. Alternatively, the first axis is a minor axis of the outer face and the second axis is a major axis of the outer face. In this manner, elliptical or oval transducers are used. Alternatively, the outer face is generally round.

In still another aspect, the transducer element further includes a second face spaced apart from the outer face to define a transducer thickness therebetween. In one aspect, the second and outer faces are both curved so that the transducer thickness is generally uniform. Alternatively, the transducer thickness varies by having the outer face curved relative to the second face.

In one aspect, the imaging assembly further includes a matching layer having first and second faces defining a matching layer thickness therebetween. Matching layer second face is coupled to the transducer element outer face. In one aspect, the matching layer thickness is generally uniform. Alternatively, the matching layer first face is generally flat so that the matching layer thickness varies. In one particular aspect, the matching layer thickness increases from a center of the transducer element to a periphery of the transducer element.

The present invention further provides an ultrasound imaging assembly including a housing having a distal end, a proximal end and a longitudinal axis. A transducer element having a generally elliptical outer face, defining a major axis and minor axis thereof, is coupled to the housing. The outer face has a first radius of curvature along the minor axis and a second radius of curvature along the major axis. The second radius of curvature is greater than the first radius of curvature so that the focussing effect along the minor axis is more enhanced than the focussing effect along the major axis. The transducer element is operably attached to the distal end to position the minor axis to be generally co-axial with the longitudinal axis.

The present invention firther provides ultrasound imaging catheters having an imaging assembly which includes a housing as previously described. A transducer element is provided having an outer face with a first radius of curvature along a first axis and a second radius of curvature along a second axis. The transducer element is mounted to the distal end to position the first axis to be generally parallel to the longitudinal axis. The catheter includes a drive cable coupled to the proximal end and a sheath into which the imaging assembly and drive cable are disposed. In one particular aspect, the sheath includes polyethylene.

In one aspect, the second radius of curvature is greater than the first radius of curvature, the first axis is a minor axis of the outer face, and the second axis is a major axis of the outer face. Alternatively, the first axis is a major axis of the outer face and the second axis is a minor axis of the outer face.

Other features and advantages of the invention will appear from the following description in which the preferred embodiment has been set forth in detail in conjunction with the accompanying drawings.

DESCRIPTION OF THE SPECIFIC EMBODIMENTS

Figure 3A:
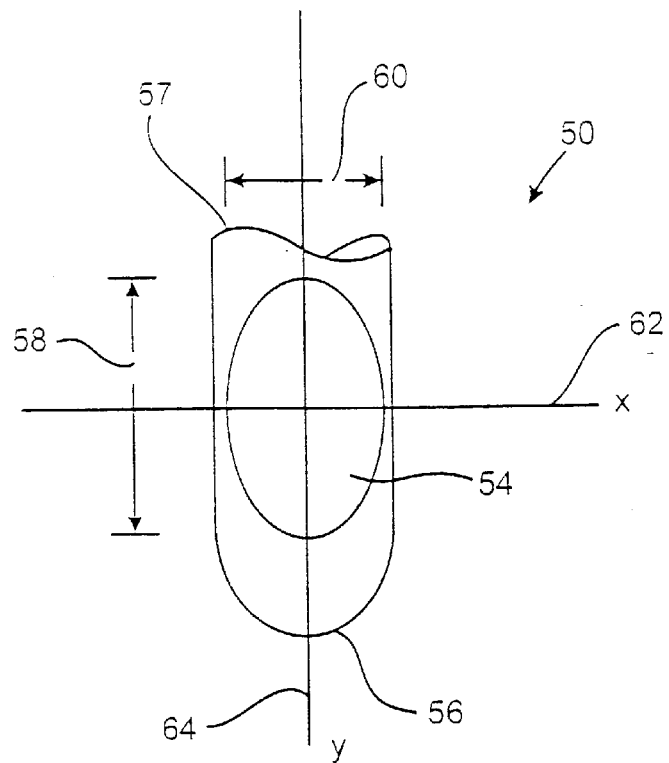
FIG. 3A depicts a top view of an exemplary imaging assembly according to the present invention.

FIG. 3A depicts an exemplary imaging assembly 50 according to the present invention. Imaging assembly 50 has a distal end 56 and a proximal end 57. Proximal end 57 is adapted to be operably attached to a drive cable (not shown). Exemplary drive cables are described in U.S. application Ser. No. 09/017,578, entitled "Integrated Coaxial Transmission Line and Flexible Drive Cable", the complete disclosure of which is incorporated herein by reference. The drive cable rotates imaging assembly 50 during operation.

A transducer element 54 is operably attached to distal end 56. Transducer element 54 may include a backing material (not shown) and one more matching layers (not shown) operably attached to opposing surfaces of transducer element 54. Transducer element 54 is generally elliptical or oval shaped, and has a major axis 58 and a minor axis 60.

During rotation of imaging assembly 50, transducer 54 projects ultrasound signals into a 360 degree image plane. The image plane has an in-plane or X-plane component 62 created primarily by the rotation of transducer 54. The image plane also has a cross-plane or Y-plane component 64 created primarily by the length of major axis 58 of transducer 54.

Figure 3B:
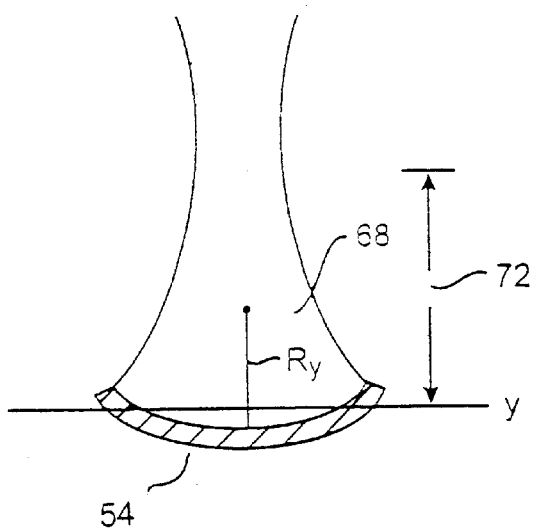
FIGS. 3B–3C depict cross-sectional side and cross-sectional front views, respectively, of the transducer included in the embodiment shown in FIG. 3A.
Figure 3C:
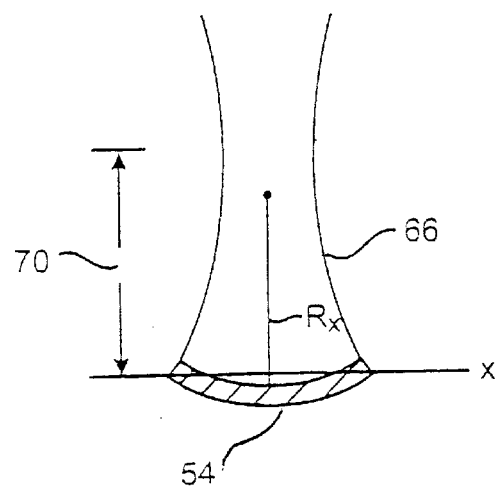

As shown in FIGS. 3B and 3C, transducer element 54 has a first radius of curvature (ROC) 68 along major axis 58, and a second ROC 66 along minor axis 60. As shown, ROC 68 is smaller than ROC 66. In other words, the radius of curvature along minor axis 60 is greater than the radius of curvature along major axis 58. As a result, major axis 58 has a tighter focus due to the smaller radius of curvature. In one particular embodiment, ROC 68 is about 2.5 millimeters (mm) and ROC 66 is about 4.0 mm, although other ROCs may be used within the scope of the present invention.

Figure 2A:
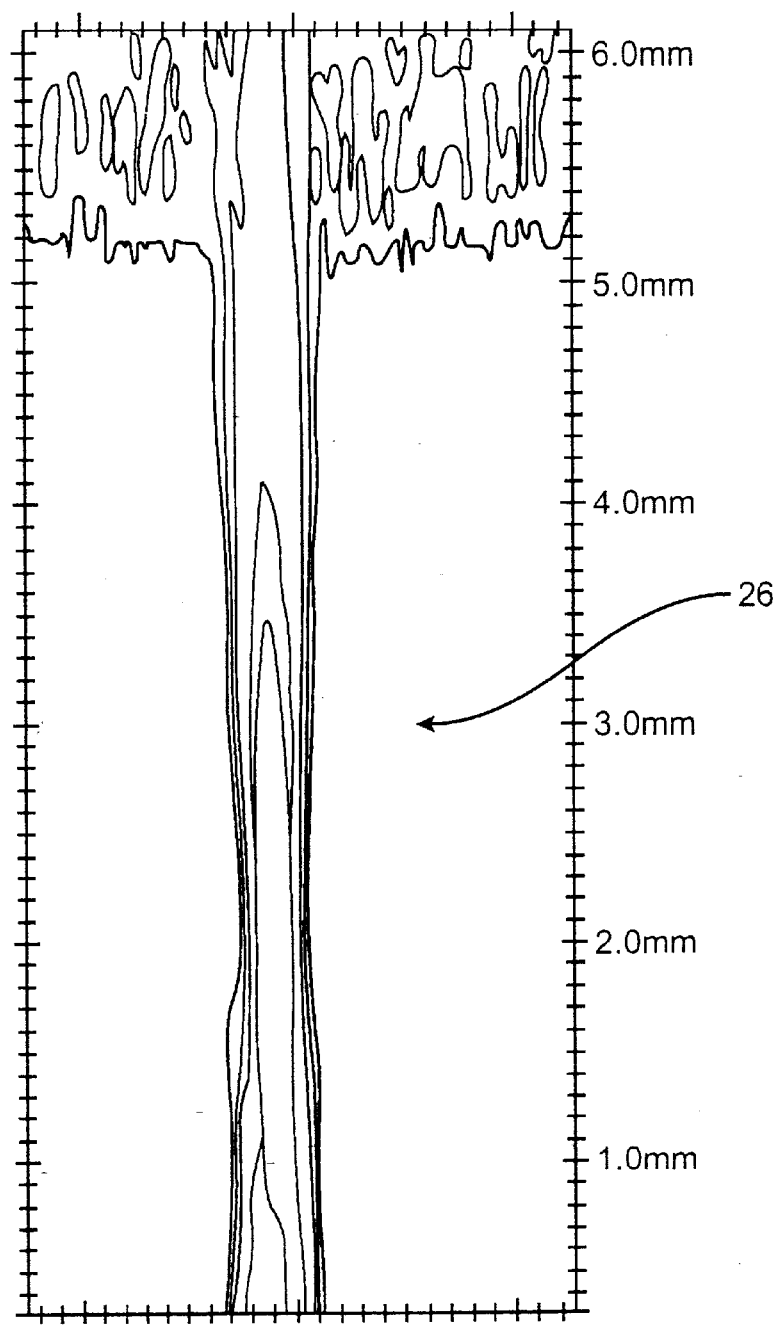
FIGS. 2A–2B depict an in-plane profile and a cross-plane profile, respectively, of the imaging catheter shown in FIGS. 1A and 1C.

Similarly, transducer 54 has a focal length 70 for X-plane component 62 and a focal length 72 for Y-plane component 64. Typically the focal length of a transducer element is a function of the transducer element size and the frequency of signals transmitted therefrom. Curving transducer element 54 provides a focusing effect. By having a tighter radius of curvature along major axis 58, the focal length of transducer 54 in the cross-plane and in-plane can be generally equal notwithstanding the larger major axis length. In one embodiment, the cross-plane and in-plane focal lengths are between about 0.25 mm and about 2.5 mm. As a result, the imaging profile in both the cross-plane and in-plane are similar to that depicted in FIG. 2A.

Figure 4:
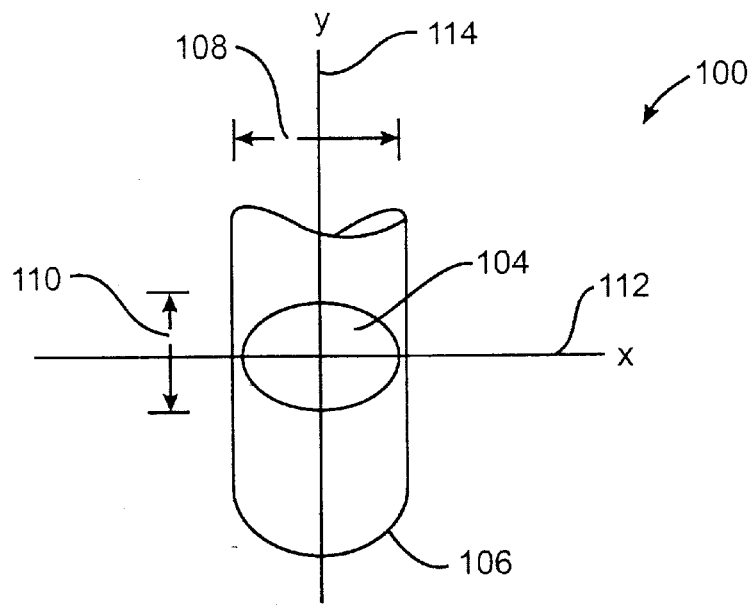
FIG. 4 depicts the top view of an alternative imaging assembly according to the present invention.

Turning now to FIG. 4, another exemplary embodiment of the present invention will be described. FIG. 4 depicts an imaging assembly 100 with a transducer element 104 operably attached to a distal end 106 of the imaging assembly 100. Transducer element 104 has a major axis 108 and a minor axis 110. In one embodiment, major axis 108 is about 0.029 inches and minor axis 110 is about 0.025 inches, although other dimensions may be used within the scope of the present invention. Transducer element 104 has a generally flat outer face.

Figure 2B:
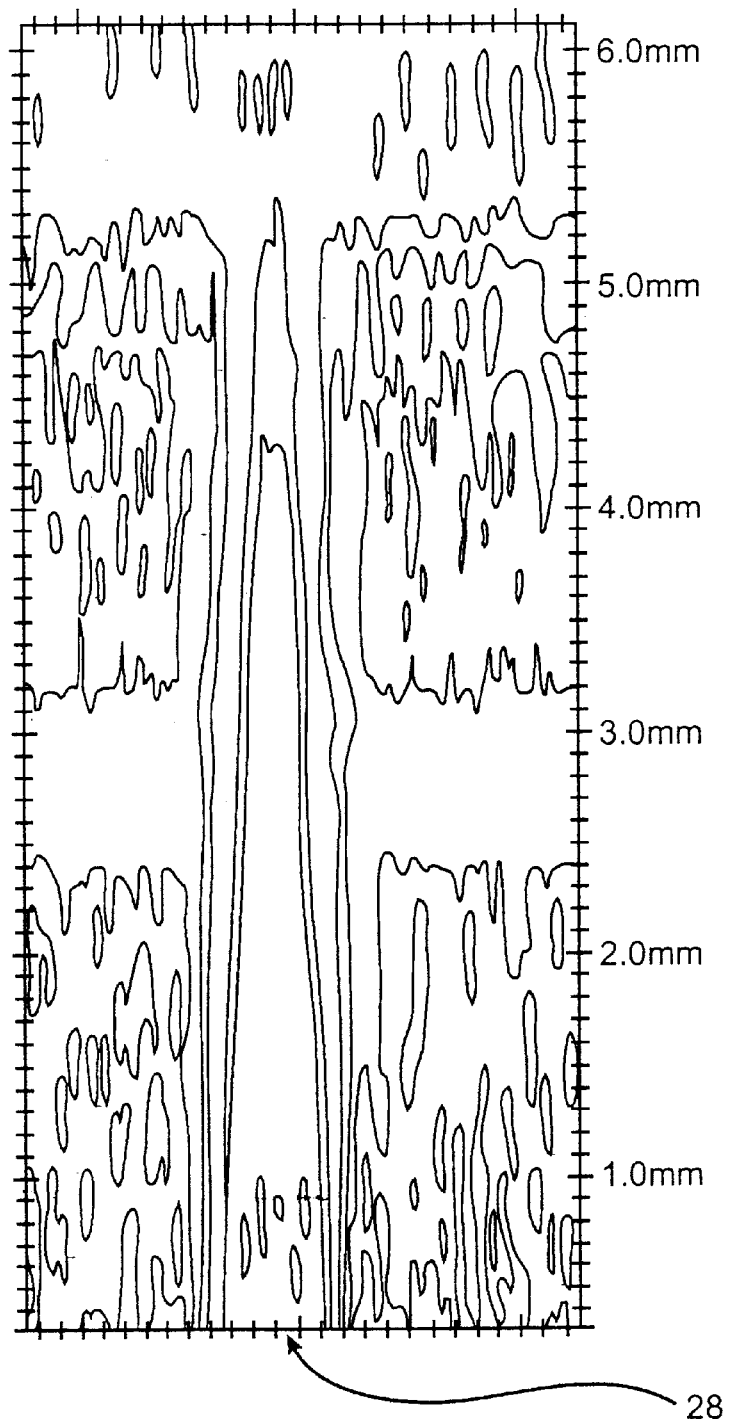

Imaging assembly 100 is rotated by a drive cable (not shown) as previously discussed. During rotation of imaging assembly 100, transducer 104 projects ultrasound signals into a 360 degree image plane. The image plane has an in-plane or X-plane component 112 created primarily by the rotation of transducer 104, and a cross-plane or Y-plane component 114 created primarily by the length of minor axis 110. In this embodiment, major axis 108 is aligned with in-plane 112, and minor axis 110 is aligned with cross-plane 114. Aligning the shorter, minor axis 110 of transducer 104 with the cross-plane compensates for at least some of the refractory effects of the sheath (not shown). As a result, ultrasound signals propagated into cross-plane 114 will have a tighter profile and a shorter focal length compared to those depicted in FIG. 2B. Hence, assembly 100 produces a more symmetrical beam profile than that depicted in FIG. 2.

In another embodiment, transducer 104 has a curved outer face. For example, transducer 104 can have a relatively uniform radius of curvature throughout. As with the embodiment described above with the flat transducer outer face, this embodiment relies primarily on the coaxial alignment of minor axis 110 with the imaging assembly longitudinal axis to provide improved cross-plane resolution. Further, the beam profile is narrowed in both the in-plane and cross-plane directions by having a curved transducer outer face with a relatively uniform radius of curvature, compared to transducer 104 having a flat outer face.

In still another embodiment, transducer 104 has a radius of curvature profile similar to that described in conjunction with FIG. 3. In this embodiment, however, minor axis 110 has a tighter radius of curvature than the major axis 108 radius of curvature. In this manner, the cross-plane component 114 of the image plane has improved resolution due to minor axis 110 being generally aligned with the imaging assembly 100 longitudinal axis, and also due to minor axis 110 having a tighter radius of curvature profile.

Figure 5A:
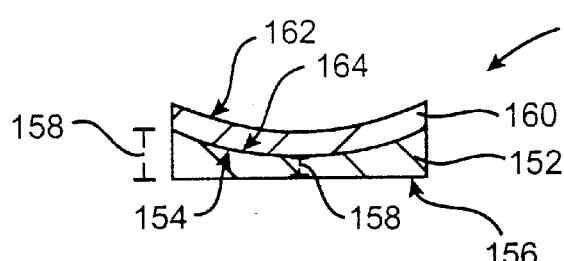
FIGS. 5A–5E depict alternative embodiments of a transducer and matching layer package for use in imaging assemblies of the present invention.
Figure 5B:
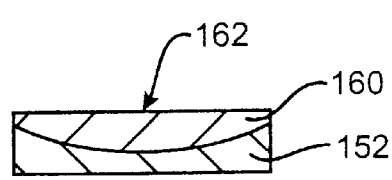
Figure 5D:
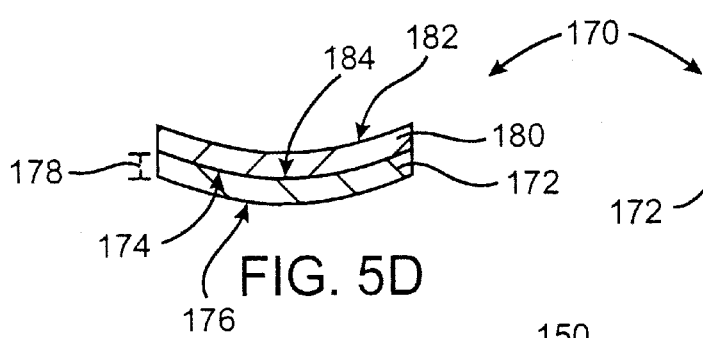
Figure 5E:
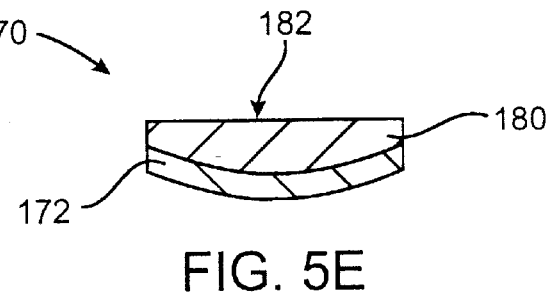
Figure 5C:
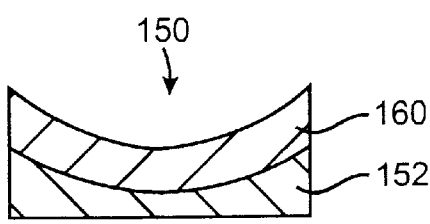

Turning now to FIGS. 5A–5E, exemplary transducer elements and matching layers for use with the present invention will be described. FIGS. 5A–5C depict a tapered focus transducer package 150. Transducer package 150 includes a transducer 152 having an outer face 154 and a second face 156. Outer face 154 and second face 156 are spaced apart to create a transducer thickness 158. As shown in FIGS. 5A–5C, outer face 154 is curved relative to second face 156. As a result, transducer thickness 158 varies across the transducer. Transducers of this type show an increase in bandwidth as compared to similar transducers of uniform thickness. FIGS. 5A–5C further include a matching layer 160 having a matching layer first face 162 and a matching layer second face 164. Matching layer second face 164 is operably attached to transducer outer face 154 using epoxy or the like.

In the embodiment shown in FIG. 5A, matching layer 160 has a generally uniform thickness. In this manner, matching layer first face 162 and matching layer second face 164 have a similar curvature to that of transducer outer face 154.

Alternatively, and as shown in FIG. 5B, matching layer first face 162 is generally flat. As a result, matching layer 160 thickness varies, with matching layer 160 being thickest near the center. Due to the diminutive sizes of transducer 152 and matching layer 160 for imaging catheters, a variable thickness matching layer 160 will likely not have severe detrimental effects to imaging performance as a result of varying thickness across matching layer 160. Further, it may be easier to manufacture matching layer first face 162 to be flat. Another embodiment, as shown in FIG. 5C, has matching layer 160 which is tapered and increases in thickness from the center of transducer element 152 towards the edge or periphery of transducer element 152 in the same fashion as the thickness of transducer element 152. The thickness of matching layer 160 varies in this embodiment so that the ratio of the matching layer 160 thickness to the thickness of transducer element 152 remains generally constant, or close to constant, throughout the transducer face 154.

As shown in FIGS. 5D–5E, a true focus transducer package 170 can be used with the imaging assemblies of the present invention, including imaging assemblies 50, 100. FIGS. 5D–5E depict a true focus transducer 172 having an outer face 174 and a second face 176. Faces 174, 176 are spaced apart from one another to define a transducer thickness 178. For true focus transducer package 170, transducer thickness 178 is generally uniform across transducer 172. FIGS. 5D and 5E further include a matching layer 180 having a matching layer first face 182 and a matching layer second face 184. Matching layer second face 184 is operably attached to transducer outer face 174 using an epoxy or the like. Again, matching layer 180 may have a uniform thickness (as shown in FIG. 5D) or a variable thickness (as shown in FIG. 5E).

Matching layers 160, 180 may comprise a wide range of materials, and preferably have an acoustic impedance less than the acoustic impedance of transducer 162, 172, respectively. Such matching layers 160, 180 help facilitate acoustic coupling with the tissue or fluid to be imaged. Matching layers of the present invention also may include a thermoplastic, as described in further detail in U.S. application Ser. No. 09/358,495, entitled "Off-Aperture Electrical Connect Transducer and Methods of Making," the complete disclosure of which is incorporated herein by reference.

Figure 6:
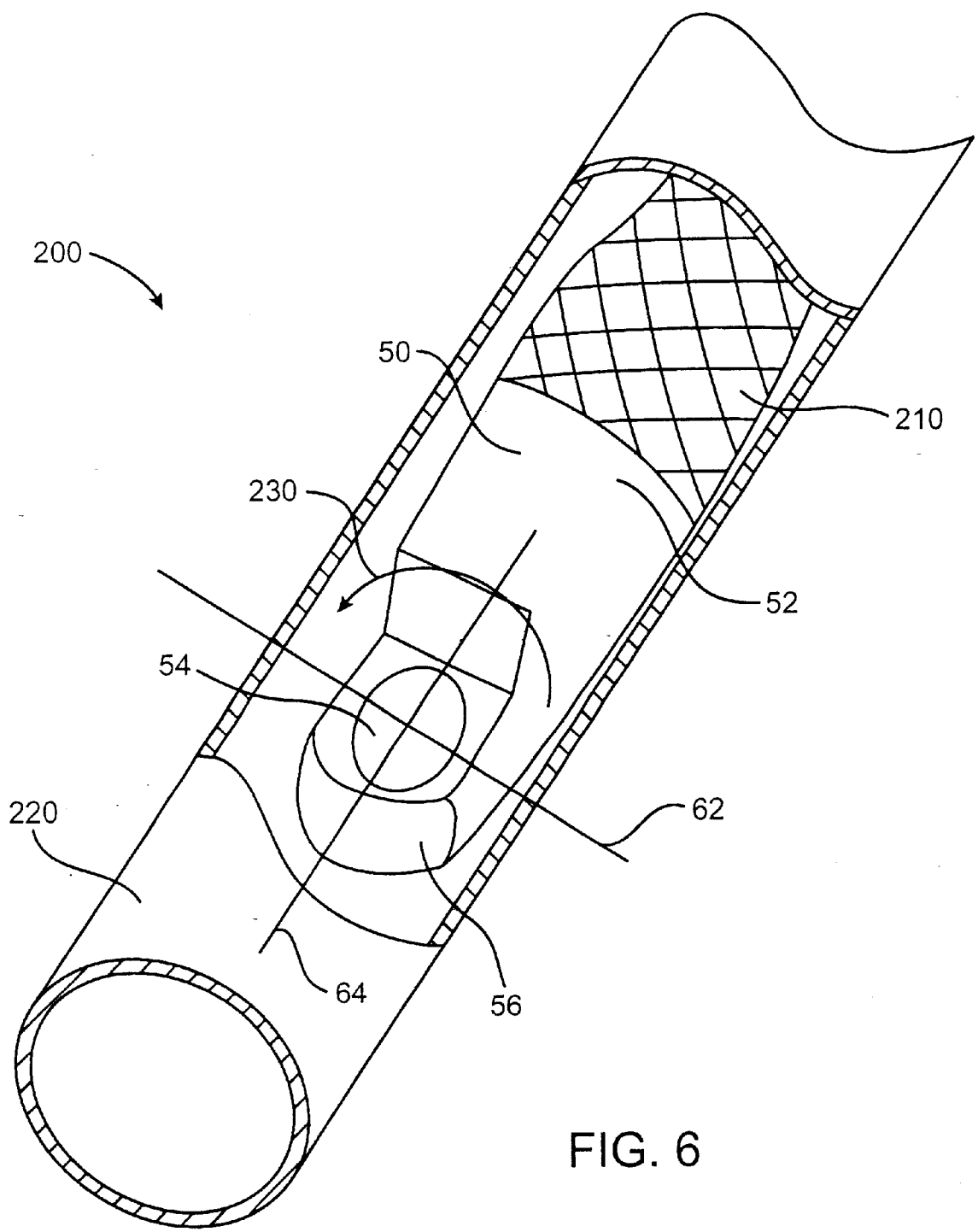
FIGS. 6–8 depict exemplary imaging catheters according to the present invention.

Turning now to FIG. 6, an exemplary imaging catheter 200 according to the present invention will be described. Catheter 200 includes an imaging assembly as previously described. Catheter 200 is depicted with imaging assembly 50, including transducer element 54 having a radius of curvature profile as previously described. However, it will be appreciated by those skilled in the art that imaging assembly 100, and other imaging assemblies, may be used with catheter 200 within the scope of the present invention.

Figure 1A:
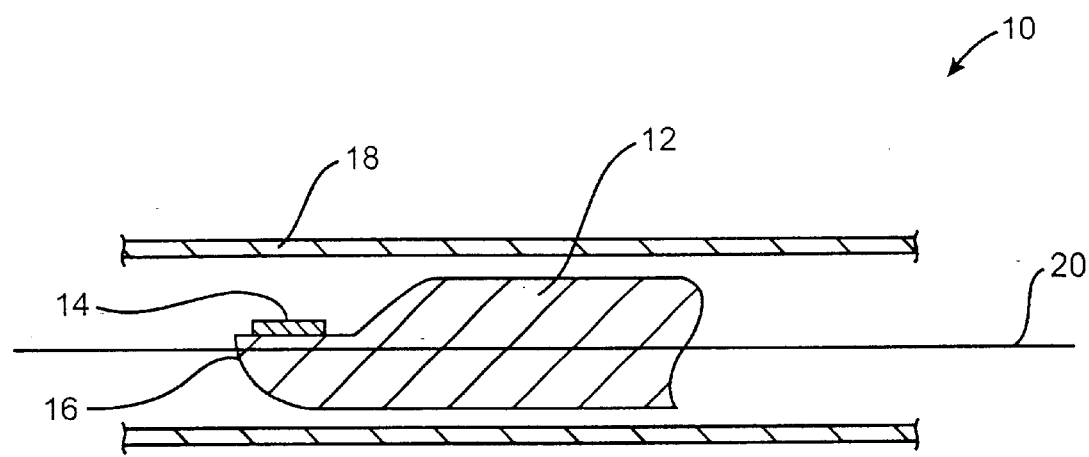
FIG. 1A provides a side cross-sectional view of a prior art imaging catheter.
Figure 1B:
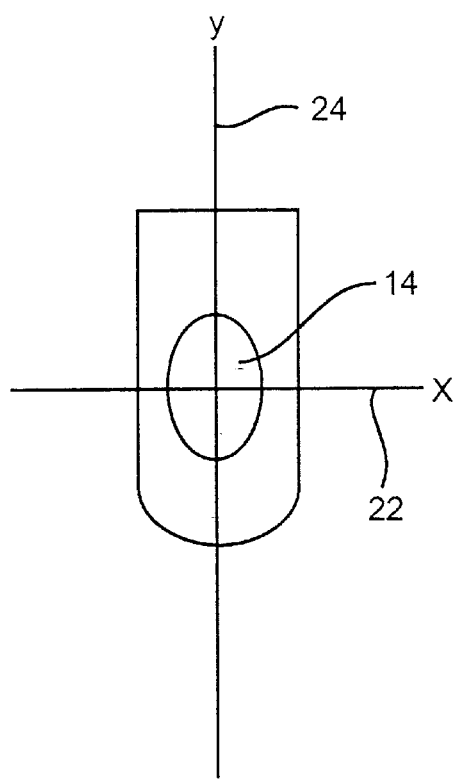
FIGS. 1B and 1C provide alternative side cross-sectional views of the prior-art imaging catheter of FIG. 1A.
Figure 1C:
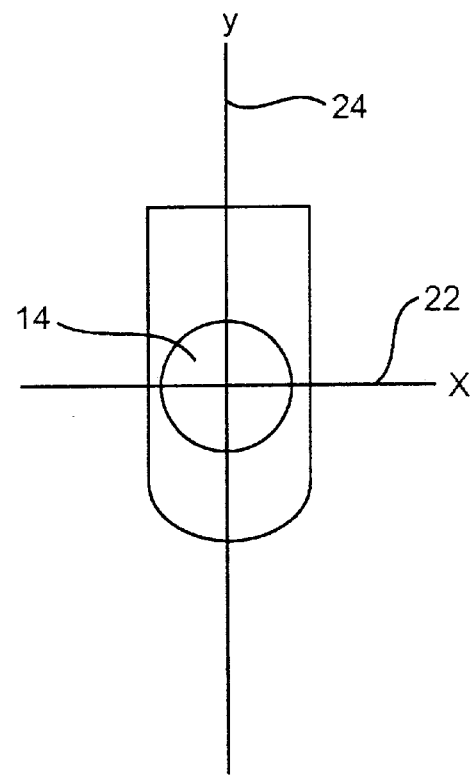

Imaging assembly 50, as described hereinbefore in greater detail, is operably attached to a drive cable 210 for rotation of imaging assembly 50. Imaging assembly 50 and drive cable 210 are disposed within a sheath 220. In one embodiment, sheath 220 comprises polyethylene of high density, low density, combinations thereof, and the like. Preferably, sheath 220 has an acoustic impedance similar to the surrounding tissue or fluids being imaged to reduce the effects of reflected signals off of sheath 220. Drive cable 210 rotates during operation of transducer 54, as shown by an arrow 230. Transducer 54 propagates ultrasound signals into an image plane having an in-plane component 62 and a cross-plane component 64. Due in part to transducer 54 having a tighter radius of curvature in the cross-plane direction, the cross-plane component 64 has improved lateral resolution compared to the assembly depicted in FIGS. 1A–1B.

Alternatively, in another embodiment, catheter 200 includes imaging assembly 100 as described in conjunction with FIG. 4. In this manner, catheter 200 has improved cross-plane lateral resolution, compared to the assembly depicted in FIGS. 1A–1B, due to the alignment of transducer 104 minor axis 110 with the longitudinal axis of catheter 200. By also providing transducer 104 with a tighter ROC in the cross-plane direction than in the in-plane direction, cross-plane lateral resolution is further improved.

Figure 7:
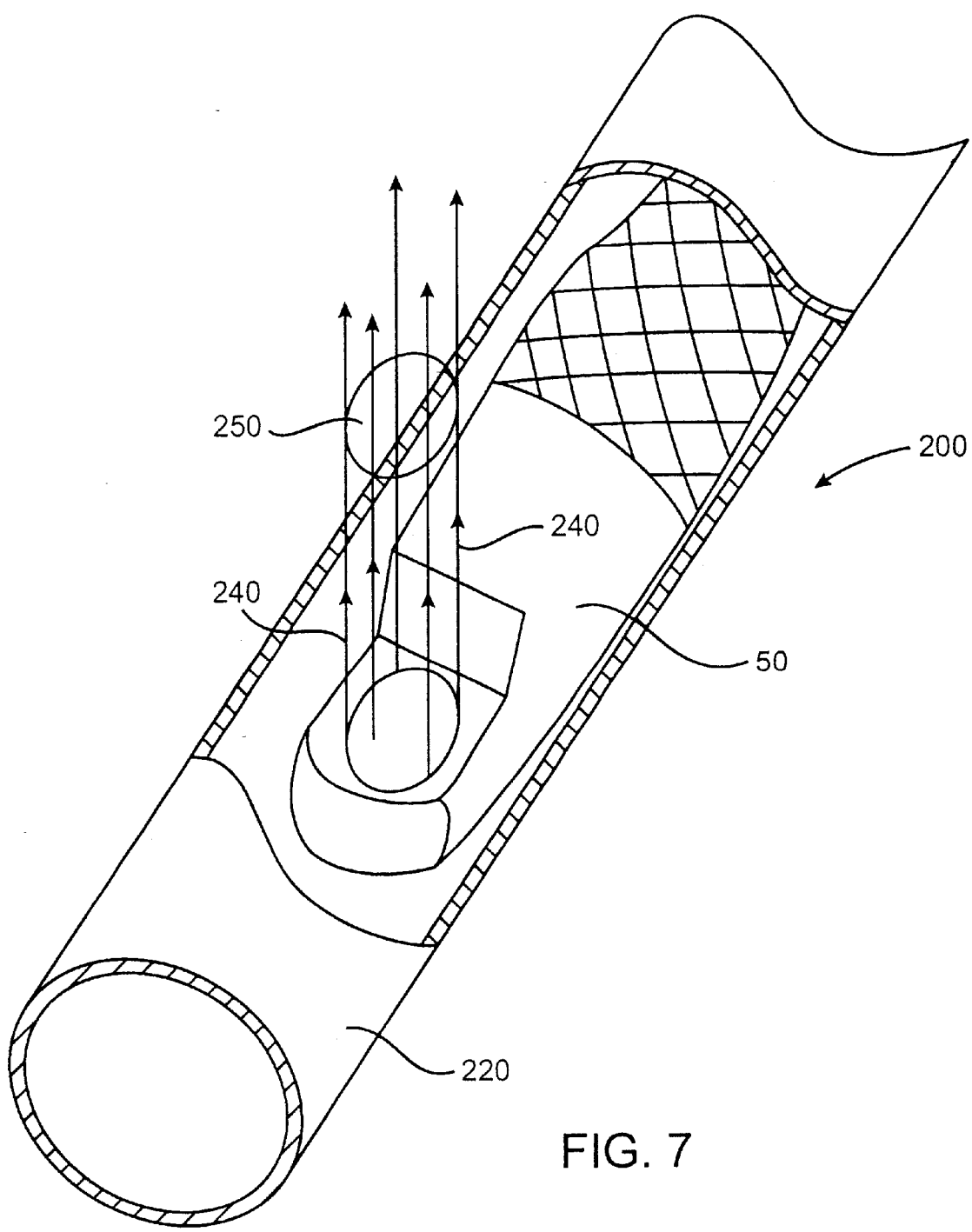

As shown in FIG. 7, the use of imaging assembly 50 having transducer 54 with the desired radius of curvature profile results in a generally circular focal plane 250. More specifically, the tighter radius of curvature of transducer 54 in the cross-plane direction, and/or having the minor axis of the transducer being parallel to the longitudinal axis of the catheter, tightens the cross-plane ultrasound profile a sufficient amount so that the focal length in the cross-plane direction and the focal length in the in-plane direction are generally equal. As a result, a tighter and more uniform ultrasound beam profile is produced.

Figure 8:
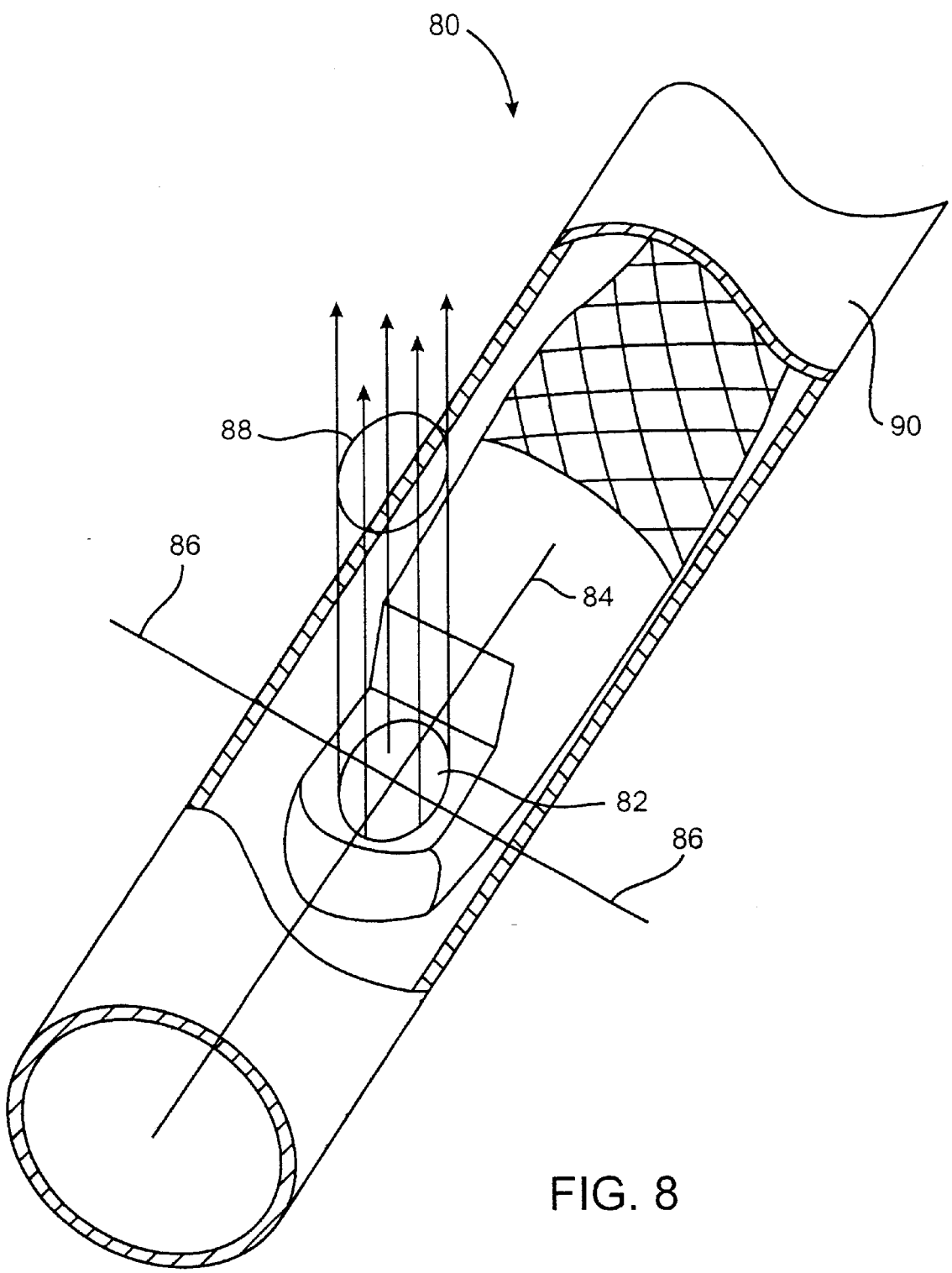

FIG. 8 depicts still another embodiment of the present invention. FIG. 8 depicts an imaging catheter 80, ostensibly as described in conjunction with FIGS. 6 and 7, except catheter 80 has a transducer element 82 having a generally round outer face. In this embodiment, transducer element 82 has a tighter radius of curvature in the cross-plane direction 84 than in the in-plane direction 86. The beam profile generated by transducer element 82 is narrowed in the cross-plane direction a sufficient amount to compensate for at least some of the beam profile widening effects of a sheath 88. In this manner, catheter 80 produces a beam profile having a generally circularly cross sectional shape at a focal plane 90.

The invention has now been described in detail. However, it will be appreciated that certain changes and modifications may be made. For example, the above description involves single transducer element imaging assemblies when the present invention is not so limited. Those skilled in the art will recognize that imaging assemblies having multiple transducer elements, including annular arrays, are within the scope of the present invention. Exemplary annular arrays are described in U.S. patent application Ser. No. 09/017,581, the complete disclosure of which is incorporated herein by reference. Therefore, the scope and content of this invention are not limited by the foregoing description. Rather, the scope and content are to be defined by the following claims.

What is claimed is:

1. An ultrasound imaging assembly comprising:
   a housing having a distal end, a proximal end, an outer surface, and a longitudinal axis; and
   a transducer element operably attached to said outer surface at said distal end, said transducer element having a generally elliptical outer face defining a major axis and a minor axis;
   said transducer element operably attached to said distal end to position said minor axis to be generally parallel to said longitudinal axis;
   said imaging assembly adapted for use in an imaging catheter.

2. An imaging assembly as in claim 1, wherein said outer face is generally oval-shaped.

3. An imaging assembly is in claim 1, wherein said outer face is generally flat.

4. An imaging assembly as in claim 1, wherein said outer face has a first radius of curvature along said minor axis and a second radius of curvature along said major axis.

5. An imaging assembly as in claim 4 wherein said second radius of curvature is greater than said first radius of curvature.

6. An imaging assembly as in claim 4, wherein said second radius of curvature is generally equal to said first radius of curvature.

7. An imaging assembly as in claim 1, wherein said proximal end is adapted to be coupled to a drive cable.

8. An imaging assembly as in claim 1, further comprising a matching layer operably attached to said outer face.

9. An imaging assembly as in claim 1, wherein said transducer element comprises a tapered focus transducer element.

10. An imaging assembly as in claim 1, wherein said transducer element comprises a true focus transducer element.

11. An imaging assembly as in claim 1, wherein said transducer element comprises a material selected from a group of materials consisting of piezoplastics, piezocomposites and piezoceramics.

12. An imaging assembly as in claim 1, wherein said transducer element is adapted to propagate an ultrasound signal in response to electrical input, said signal comprising an in-plane signal component that is generally perpendicular to said longitudinal axis and a cross-plane signal component that is generally parallel to said longitudinal axis, said in-plane signal component having an in-plane focal length that is generally equal to a cross-plane focal length of said cross-plane signal component.

13. An imaging assembly as in claim 12, wherein said in-plane focal length is between about 0.25 mm and about 2.5 mm, and said cross-plane focal length is between about 0.25 mm and about 2.5 mm.

14. An imaging assembly as in claim 12, wherein said outer face has a shape and a radius of curvature profile so that said ultrasound signal has a generally circular cross sectional shape at a prescribed distance from said distal end.

15. An ultrasound imaging assembly comprising:
   a housing having a distal end, a proximal end, and a longitudinal axis; and
   a transducer element having an outer face, said outer face having a first radius of curvature along a first axis and a second radius of curvature along a second axis;
   said transducer element being operably attached to said distal end to position said first axis to be generally parallel to said longitudinal axis.

16. An imaging assembly as in claim 15, wherein said second radius of curvature is greater than said first radius of curvature.

17. An imaging assembly as in claim 16, wherein said first axis is a major axis of said outer face and said second axis is a minor axis of said outer face.

18. An imaging assembly as in claim 16, wherein said outer face is generally round.

19. An imaging assembly as in claim 15, wherein said first axis is a minor axis of said outer face and said second axis is a major axis of said outer face.

20. An imaging assembly as in claim 19, wherein said first radius of curvature is about equal to said second radius of curvature.

21. An imaging assembly as in claim 19, wherein said second radius of curvature is greater than said first radius of curvature.

22. An imaging assembly as in claim 15, wherein said transducer element further comprises a second face spaced apart from said outer face, said outer face and said second face defining a transducer thickness therebetween.

23. An imaging assembly as in claim 22, wherein said outer face and said second face are both curved so that said transducer thickness is generally uniform.

24. An imaging assembly as in claim 22, wherein said outer faced is curved relative to said second face so that said transducer thickness varies.

25. An imaging assembly as in claim 15 further comprising a matching layer having first and second faces defining a matching layer thickness therebetween, said matching layer second face being coupled to said transducer element outer face.

26. An imaging assembly as in claim 25, wherein said matching layer first face is generally flat so that said matching layer thickness varies.

27. An imaging assembly as in claim 25 wherein said matching layer first face is curved so that said matching layer thickness is generally uniform.

28. An imaging assembly as in claim 25, wherein said matching layer is concave and said matching layer thickness increases from a center of said transducer element towards a periphery of said transducer element.

29. An ultrasound imaging assembly comprising:
a housing having a distal end, a proximal end, and a longitudinal axis; and
a transducer element having a generally elliptical outer face, said outer face defining a major axis and a minor axis and having a first radius of curvature along said minor axis and a second radius of curvature along said major axis, said second radius of curvature being greater than said first radius of curvature;
said transducer element being operably attached to said distal end to position said minor axis to be generally coaxial with said longitudinal axis.

30. An ultrasound imaging catheter comprising:
an imaging assembly comprising,
a housing having a distal end, a proximal end, and a longitudinal axis; and
a transducer element having an outer face, said outer face having a first radius of curvature along a first axis and a second radius of curvature along a second axis, said transducer element being operably attached to said distal end to position said first axis to be generally parallel to said longitudinal axis;
a drive cable coupled to said proximal end; and
a sheath into which said imaging assembly and drive cable are disposed.

31. An imaging catheter as in claim 30, wherein said sheath comprises polyethylene.

32. An imaging catheter as in claim 30, wherein said second radius of curvature is greater than said first of curvature, said first axis is a minor axis of said outer face, and said second axis is a major of said outer face.

33. An imaging catheter as in claim 30, wherein said second radius of curvature is greater than said first radius of curvature, said first axis is a major axis of said outer face, and second is a minor axis of said outer face.

* * * * *

UNITED STATES PATENT AND TRADEMARK OFFICE
CERTIFICATE OF CORRECTION

PATENT NO.   : 6,287,261 B1
DATED        : September 11, 2001
INVENTOR(S)  : Veijo T. Suorsa, Dennis Mendoza and Richard Bautista It is certified that error appears in the above-identified patent and that said Letters Patent is hereby corrected as shown below:

Claim 15,
Lines 41-46,
      a transducer element having an outer face, said outer face having a first radius of curvature along a first axis and a second radius of curvature along a second axis, said first radius of curvature being different than said second radius of curvature;
      said transducer element being operably attached to said distal end to position said first axis to be generally parallel to said longitudinal axis.

Claims 32 and 33,
Lines 21-28,
      32.    An imaging catheter as in claim 30, wherein said second radius of curvature is greater than said first radius of curvature, said first axis is a minor axis of said outer face, and said second axis is a major axis of said outer face.
      33.    An imaging catheter as in claim 30, wherein said second radius of curvature is greater than said first radius of curvature, said first axis is a major axis of said outer face, and said second axis is a minor axis of said outer face.

Signed and Sealed this

Ninth Day of April, 2002

Attest:

JAMES E. ROGAN
*Director of the United States Patent and Trademark Office*

*Attesting Officer*